(12) United States Patent
Barefoot

(10) Patent No.: US 10,279,089 B1
(45) Date of Patent: *May 7, 2019

(54) WOUND CANISTER WASTE SOLIDIFICATION SYSTEM

(71) Applicant: Stewart Superabsorbents, LLC, Hickory, NC (US)

(72) Inventor: Quint Barefoot, McLeansville, NC (US)

(73) Assignee: Stewart Superabsorbents, LLC, Hickory, NC (US)

( * ) Notice: Subject to any disclaimer, the term of this patent is extended or adjusted under 35 U.S.C. 154(b) by 188 days.

This patent is subject to a terminal disclaimer.

(21) Appl. No.: 15/293,360

(22) Filed: Oct. 14, 2016

Related U.S. Application Data

(63) Continuation of application No. 14/202,377, filed on Mar. 10, 2014, now Pat. No. 9,533,081.

(60) Provisional application No. 61/776,242, filed on Mar. 11, 2013.

(51) Int. Cl.
*A61M 1/00* (2006.01)

(52) U.S. Cl.
CPC ........ *A61M 1/0096* (2014.02); *A61M 1/0088* (2013.01)

(58) Field of Classification Search
CPC .............. A61M 1/0001; A61M 1/0088; A61M 1/0094; A61M 1/0096; A61M 2205/0272; A61M 2209/088
See application file for complete search history.

(56) References Cited

U.S. PATENT DOCUMENTS

| | | | |
|---|---|---|---|
| 2,671,602 A | 9/1948 | Vogt | |
| 4,415,236 A | 11/1983 | Perregaux | 350/338 |
| 4,748,069 A | 5/1988 | Cullen | 428/195.1 |
| 4,749,600 A | 6/1988 | Cullen et al. | 428/34.3 |
| 4,853,266 A * | 8/1989 | Cullen | B65D 65/46 206/204 |
| 5,007,116 A * | 4/1991 | Yamamoto | A61F 5/4556 4/144.2 |
| 5,092,858 A | 3/1992 | Benson et al. | 604/319 |
| 5,234,419 A | 8/1993 | Bryant | 137/205 |
| 5,284,621 A | 2/1994 | Kaufman | 422/32 |
| 5,391,351 A | 2/1995 | Kaufman | 422/28 |
| 5,424,265 A | 6/1995 | Weinstein | 502/400 |
| 5,635,196 A | 6/1997 | Murphy | 424/409 |
| 6,797,857 B2 | 9/2004 | Tanhehco | 604/368 |
| 7,291,674 B2 | 11/2007 | Kang et al. | 525/54.1 |
| 8,257,328 B2 | 9/2012 | Augustine et al. | 604/313 |
| 8,333,744 B2 | 12/2012 | Hartwell et al. | 604/319 |
| 8,450,389 B1 | 5/2013 | Barefoot | 523/122 |
| 9,533,081 B1 * | 1/2017 | Barefoot | A61M 1/0094 |
| 2002/0185156 A1 | 12/2002 | Tanhehco | 134/6 |
| 2003/0097100 A1 * | 5/2003 | Watson | A61M 1/0001 604/320 |
| 2004/0144682 A1 | 7/2004 | Altmayer | 206/524.7 |

(Continued)

*Primary Examiner* — Adam Marcetich
(74) *Attorney, Agent, or Firm* — MacCord Mason PLLC

(57) ABSTRACT

The invention includes a negative wound therapy system including a container, a wound covering, a packet and a plurality of surface cross-linked superabsorbent particles. The invention may be portable. The invention also includes a liquid solidification system for reducing gel block in NPWT systems. Methods of solidifying liquid medical waste from NPWT devices are also described and disclosed.

20 Claims, 5 Drawing Sheets

(56) References Cited

U.S. PATENT DOCUMENTS

| | | |
|---|---|---|
| 2005/0233900 A1 | 10/2005 | Smith et al. .................. 502/407 |
| 2006/0173430 A1 | 8/2006 | Lee et al. ...................... 604/368 |
| 2007/0167560 A1 | 7/2007 | Smith ........................... 524/556 |
| 2009/0036873 A1 | 2/2009 | Nielsen et al. ............... 604/543 |
| 2011/0001087 A1 | 1/2011 | Hillebrecht .................. 252/194 |
| 2011/0172612 A1 | 7/2011 | Greener et al. .............. 604/313 |
| 2012/0209225 A1* | 8/2012 | Hu ..................... A61M 1/0066 604/319 |
| 2012/0296295 A1 | 11/2012 | Gray et al. .................... 604/369 |
| 2013/0053797 A1* | 2/2013 | Locke ................ A61M 1/0088 604/319 |

\* cited by examiner

WOUND CANISTER WASTE SOLIDIFICATION SYSTEM

This application is a Continuation of U.S. application Ser. No. 14/202,377, filed Mar. 10, 2014, which claims the benefit of U.S. provisional application No. 61/776,242, filed Mar. 11, 2013, which are incorporated herein by reference in their entireties.

BACKGROUND

This disclosure relates generally to portable negative pressure wound therapy systems and methods for treating a wound and more specifically, an improved wound canister waste solidification system.

Wound healing is known to present challenges within the medical field. In order for a wound to close, epithelial and subcutaneous tissues around the wound migrate and progress towards the center and away from the base of the wound until the wound closes. Closure is especially difficult with larger wounds, chronic wounds or wounds that have become infected. A zone of stasis (area in which localized swelling of tissue may restrict blood flow to the tissues) may form near the surface of a wound, preventing tissues from receiving adequate oxygen and nutrients and inhibiting the ability to resist microbial infection and affect proper wound healing.

Negative pressure wound therapy (NPWT), also known as suction or vacuum therapy, has been used and found beneficial in treating and healing large or difficult wounds. Applying negative pressure to an area over a wound has been found to promote closing of the wound due to promotion of blood flow to the area, stimulation of the formation of granulation tissue and encouragement of the migration of healthy tissue over the wound. Fluids may also be drawn from the wound by using negative pressure and thus remove fluids that would otherwise tend to encourage bacterial growth. Particularly, this negative pressure therapy has been recognized as effective for chronic, healing-resistant and post-operative wounds.

Typically, in NPWT, a wound covering is positioned over a wound. An attachment in communication with a vacuum source, such as tubing, is added to the wound covering and facilitates suction at the wound site. Fluids and exudates drawn off the wound site through the tubing are usually transferred to and stored in a waste storage container.

Often, it is in the best interest of a patient to remain ambulatory if possible. In such circumstances, portable NPWT devices may be prescribed for a patient with a wound. Portable NPWT devices are typically large and have attachments, such as a control unit, including a suction pump and electronic monitor, for example, microprocessors or pressure transducers. It is recognized that NPWT devices are prone to tipping and/or leakage at the container and around the wound covering, especially when portable NPWT units are worn and patients move around. This produces several problems, however. For example, the exudates may aspirate from the container and clog the attachment, damage the electronics and pump and/or leak from the container and expose the patient to biological wastes and contaminants. To address these problems, some have attempted to provide improved tubing, while others have increased the pump strength and/or improved the seal made by the wound covering at the wound site. Screens, filters and seals have been added to NPWT systems in an attempt to prevent leakage of waste fluids from the waste storage container and backflow into tubing, control and negative pressure sources.

Absorbents have even been added to containers in an attempt to limit the liquid available to spill or leak. The absorbents, typically used, however, do not reach full solidification of the fluids for many reasons. Some absorbents can also be caustic and must be very carefully handled by patients and medical personnel in order to avoid exposure. Despite these attempts to prevent potential harmful exposure, leakage of biological wastes and potentially harmful bacteria, fungi or other organisms remains a problem. The potential for spillage of these contaminants may inhibit patients from utilizing portable NPWT devices and/or prolong a hospital stay due to a wound. Home use of NPWT is discouraged when patients would have to tend to the device and contamination exposure remains a real threat. As a result, hospital stays may be prolonged unnecessarily and medical costs increased. It is to these and other problems that this disclosure is directed.

SUMMARY OF THE INVENTION

The invention of the present disclosure fulfills one or more of these needs in the art by providing in one embodiment a portable negative pressure wound therapy system including a container, a wound covering, a packet able to be housed within the container and a plurality of superabsorbent particles enclosed within the packet and releasable upon dissolution of at least a portion of the packet in aqueous liquid. The container is operable to receive fluid from a wound site. The container is also in communication with a vacuum tube. The vacuum tube connects to a control having a negative pressure source. The wound covering connects to the vacuum tube so that the negative pressure source is able to exert a negative pressure on the wound site through the covering when the covering is applied to the site. The packet is at least partially soluble in an aqueous liquid.

Additionally, the system may include a sanitizer. The sanitizer may be granular chlorine and/or any other agents that destroy bacteria, fungi, viruses and/or related organic matter.

Another embodiment includes a system for solidification of liquid medical waste for use in connection with aqueous liquid to be solidified from a NPWT device. In one example, the system includes an absorbent composition and a packet enclosing the absorbent composition. The absorbent composition is granular and includes a plurality of surface cross-linked superabsorbent particles. The absorbent composition may additionally include a plurality of second particles. The packet is at least partially soluble in the aqueous liquid to be solidified so that the absorbent composition is released upon dissolution of the packet. The packet may be made of dissolvable polyvinyl alcohol and/or the packet may include only a dissolvable portion.

In another embodiment, a liquid solidification system for reducing gel block in a NPWT system includes a packet and a solidifier. The packet is configured to allow liquid penetration. The solidifier is initially located within the packet and includes a plurality of surface cross-linked superabsorbent polymer particles. A plurality of second particles may also be included. Liquid flow channels are defined between the superabsorbent polymer particles. Second particles may also act as spacers to provide flow channels.

The invention can also be considered as a solidification method for NPWT waste fluids including the steps of connecting a container operable to receive fluid from a wound site with a NWPT device; having the container in communication with a vacuum tube; providing a negative pressure source; allowing a wound covering to connect to the vacuum tube so that the negative pressure source is able to exert a negative pressure on the wound site through the covering when the covering is applied to the site, and including a packet in the container to be housed within the container, the packet being at least partially soluble in an aqueous liquid and having a plurality of surface cross-linked superabsorbent particles enclosed within the packet that are releasable upon dissolution of at least a portion of the packet in the aqueous liquid.

The method may also include housing sanitizer along with the particles inside the packet. In another example, a method of solidification for NPWT systems includes: selecting a portion of cross-linked superabsorbent particles that maintain a state of permeability upon solidification, determining the portion based upon a volume of liquid wastes to be solidified within a NPWT container during a NPWT treatment, and housing the portion inside an at least partially soluble packet.

BRIEF DESCRIPTION OF THE DRAWINGS

The invention will be better understood by a reading of the Detailed Description of the Examples of the Invention along with a review of the drawings, in which.

DETAILED DESCRIPTION OF THE PREFERRED EMBODIMENTS

Figure 1:
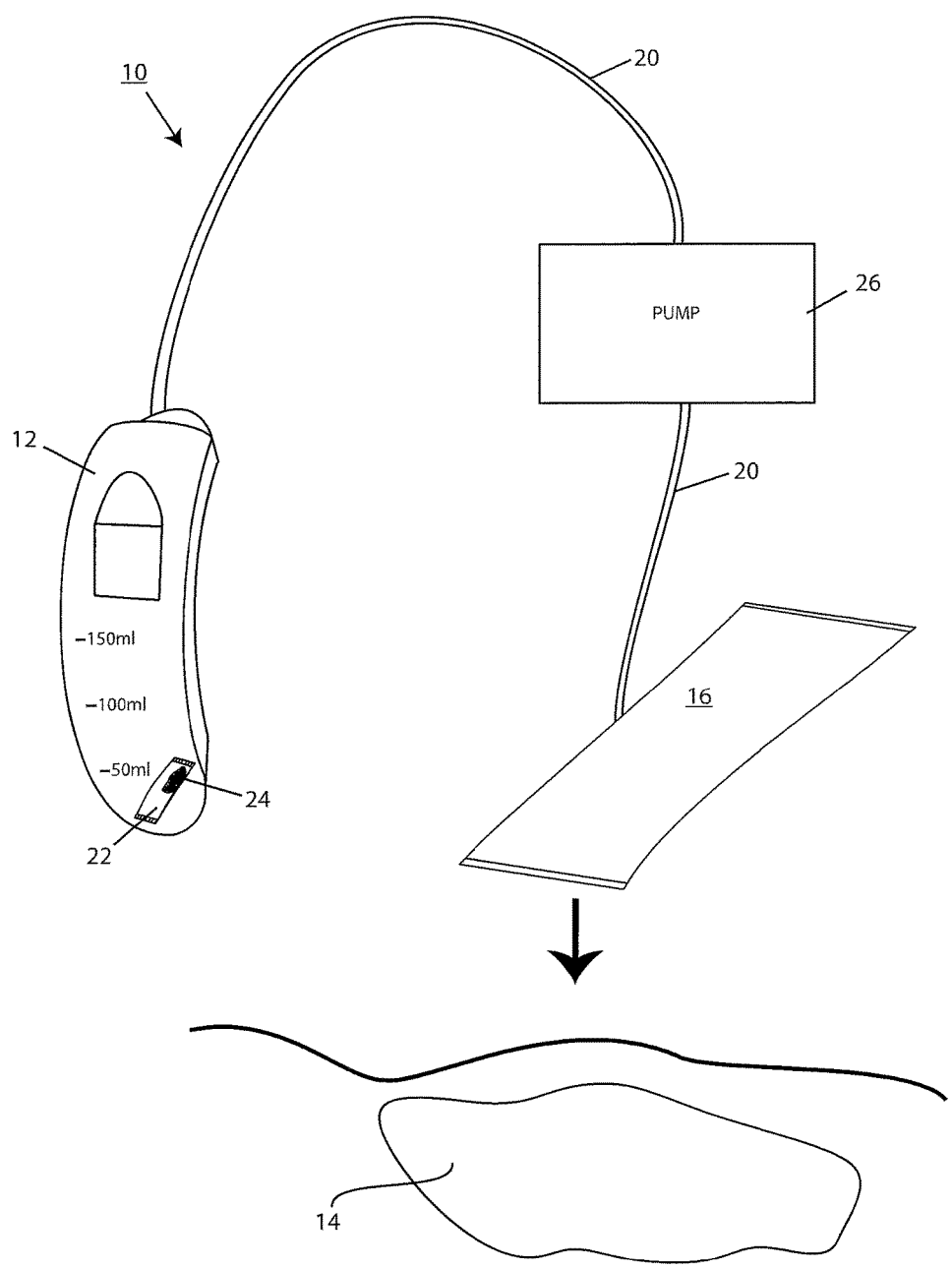
FIG. 1 is a perspective view of one example of a portable negative pressure wound therapy system.

In hospitals, collection of liquid medical waste is regulated and must be solidified prior to being transported and/or discarded. Even hospitals struggle to adequately solidify liquid wastes, such as those often gathered during surgery, in order to meet regulation and prevent patient and personnel exposure. Many waste solidifiers are contained in bottles and the solidifier must be accurately measured, depending on the amount of the waste fluids, and then administered to a waste vessel after the fluids are collected. Exposure during application of the solidifier, complicated measurements, inadequacy of the solidifiers and inconvenience prevents these hospital solidifiers from successfully being used in negative pressure would therapy, particularly portable and home NPWT.

Further, when using solidifiers for solidifying liquid wastes, reaching firm solidification is necessary so no fluids will spill when the container is turned on its side. Otherwise, some of the waste is solidified, while a portion remains liquid and prone to spillage, and provides a false sense of security and a potential health and safety threat to the operator.

"Gel block" is recognized as a problem with solidifiers, particularly when solidifier is added to a container prior to the collection of the wastes, in an attempt to limit or prevent contaminant exposure after wastes are present in the container. Development of gel block prohibits firm solidification of liquids. Gel block occurs when an inflowing aqueous mixture reaches some of the solidifier and becomes solidified but then the solidified waste sections off portions of the fluid so that it cannot reach remaining available solidifier (where portions of the liquid and available solidifier are unable to come into contact with each other), essentially creating a "block" to firm solidification. When gel block occurs, the aqueous fluid does not firmly and completely solidify, and spillage during transport or movement is problematic. Previously, the problem of gel block has been addressed in a variety of ways. Various solidifiers with different densities have been combined so that the solidifier will migrate to specific levels or zones of the fluid. However, weighted solidifiers take some time to reach their separated levels, and the use of swifter solidifiers with a NPWT system still presents problems with gel block. Additionally, the speed with which the fluid is introduced and the timing of the release of weighted solidifier is extremely important if the weighted solidifier is to inhibit gel block. Very quickly introduced and/or small amounts of fluid introduced over a longer period of at least an hour and fluid introduction persisting for hours and days increases the problems with gel block occurrence.

Absorbents contained within burstable paper pouches have been used and may actually intensify gel block in some instances because enough water must slowly seep through the pouch and create enough expansion within the absorbents to rupture the bag before the absorbent is released into the entire waste container environment. The release of absorbents in this scenario can be unpredictable and unreliable. While certain solidifiers may suffice to solidify liquid wastes during hospital procedures, such as surgeries, Applicant realized that NPWT treatments typically extends over a longer period of time than finite hospital procedures and usage of solidifiers with NPWT systems included additional challenges. With these types of recognized problems occurring with the use of solidifier in quickly disposed biological waste containers, solidifier for use in patient controlled collection devices is even more problematic, especially when solidifier needs to solidify small amounts of fluids gathered over longer periods of time, at least an hour and perhaps days or even months. Applicant's invention addresses these and other such problems and needs in the art.

Superabsorbent polymers, such as that disclosed in U.S. Pat. No. 7,291,674 to Kang, which is herein incorporated by reference in its entirety, are known as water-swellable, water-insoluble, organic or inorganic material capable of absorbing at least about 100 times its weight and up to about 300 times its weight in an aqueous solution. Superabsorbent polymers are cross-linked, neutralized polymers which are capable of absorbing large amounts of aqueous liquids and body fluids, such as urine, wound exudates or blood, with swelling and the formation of hydrogels, and of retaining them under a certain pressure in accordance with the general definition of superabsorbent. The main use for internally cross-linked superabsorbent polymers, however, has been in sanitary articles, such as diapers. The trend in sanitary articles, for comfort and sanitation reasons, has been to make them smaller and reduce their size. To do this, much of the fluff fiber in these articles has been removed and more superabsorbent polymer has been added. With less structure provided, more superabsorbent polymer is needed in sanitary articles along with a higher gel strength. However, increasing gel strength in cross-linked superabsorbent polymers often results in less polymer swellability, permeability and retention capacity. The Kang patent addresses surface cross-linking superabsorbent polymers in order to maintain liquid retention, permeability, and, particularly gel bed strength under pressure, when superabsorbent polymer is increased in percent by weight based on the dry absorbent structure.

Applicant realized that surface cross-linked superabsorbent polymer could be developed and used in aqueous environments, such as biological waste containers, where permeability and liquid solidification are the main objectives and not particularly gel bed strength. Applicant has discovered that the use of the superabsorbent polymer in NPWT systems prevents development of gel block and addresses the problems associated with NPWT devices, particularly when patients move around, have a portable NPWT device, and/or are considered for patient use outside of a hospital.

Referring now to the drawings in general, the illustrations are for the purpose of describing a preferred example of the invention and are not intended to limit the invention thereto. NPWT devices are generally known in the art. One benefit of Applicant's invention is that it inhibits free waste liquid available for spillage in a manner compatible with many, if not all, NPWT devices that shuttle the biological waste to a storage container. This is true particularly for portable NPWT devices. FIG. 1 shows one example of a portable negative pressure wound therapy system, generally referred to as 10, including a container 12 operable to receive fluid from a wound site 14, a negative pressure vacuum source 26, a wound covering 16 connecting to a vacuum tube 20, a packet 22 and a plurality of surface cross-linked superabsorbent particles 24 enclosed within the packet.

Figure 2:
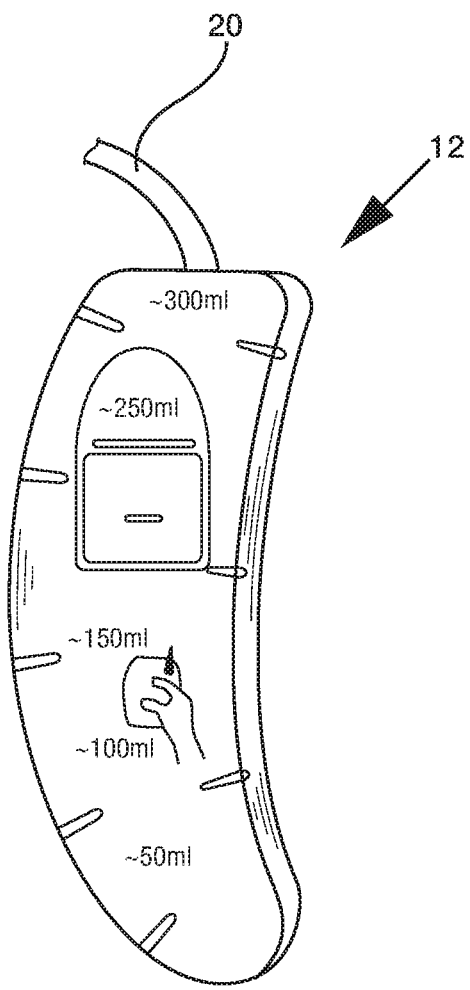
FIG. 2 is a side view of one example of a container of the portable negative pressure wound therapy system according to FIG. 1.
Figure 3:
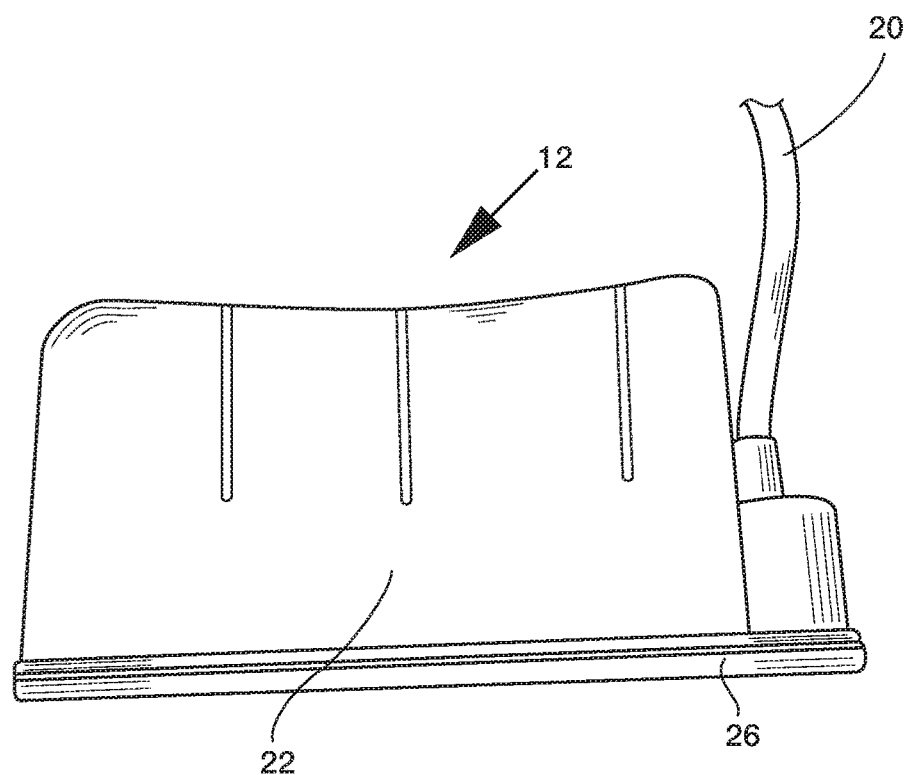
FIG. 3 a another side view of one example of a container including a packet.
Figure 5:
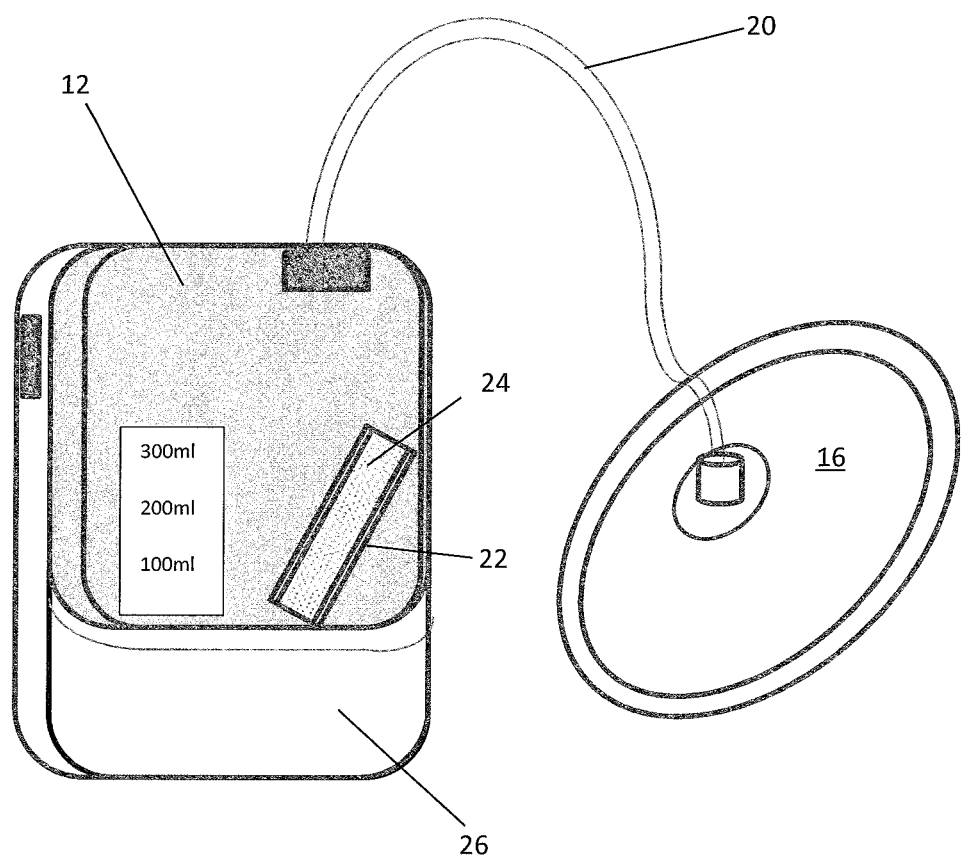
FIG. 5 is a perspective view of another example of a negative pressure wound therapy system.

The container 12 is operable to receive fluid from a wound site and is typically in communication with a vacuum tube 20. FIGS. 2 and 3 show side views of an example container. The container may include a lid 26. The container may have a compartment for storage of exudate and/or the entire container may serve as a storage compartment. Exudate and biological waste as used herein, generally refers to any fluid output from a wound, such as but not limited to, blood, serum, pus, biological contaminants, biological organisms, irrigation fluids, and/or small tissues contained within the fluids. The container may exist independently of the other NPWT devices, or it may incorporate with other NPWT devices, as seen in FIG. 5 where the container 12 fits removably onto the pump. The vacuum tube typically connects to a vacuum control having a negative pressure source 26, for example, a vacuum pump, such as a peristaltic pump, a diaphragmatic pump or a mini/micro-pump. The exudate from the wound is directed through a vacuum tube and deposited in the container. The term "tube" refers to any conduit or passageway that is suitable for transporting the exudate to the container. The container may take on variable sizes and shapes. For example, the collection container may be rigid or a semi-rigid plastic container or may be a polymeric pouch.

The wound covering 16, one example of which is described in U.S. Pat. No. 8,257,328, which is herein incorporated in its entirety, is typically connected to the vacuum tube 20 so that the negative pressure source 26 is able to exert a negative pressure on the wound site 14 through the covering when the covering is applied to the site. Wound coverings may have different dimensions to accommodate different wounds. Typically, the wound coverings are applied to the wound and sealed to create a sealed wound dressing. The dressing may include, by way of example, a port assembly, an open-cell foam wound covering, dressings and gauze, often sealed with an occlusive dressing to allow a vacuum to persist at the wound site. Dressings may also include wound cover layers and wound fillers. Wound covers may be removed from connection with the vacuum tube so that the dressing may be changed. The wound covering and/or dressing may be changed while the remainder of the NPWT system remains in place. The new wound covering may be reattached to the vacuum tube and the NPWT treatment resumed. It is not uncommon for wound coverings and/or entire wound dressings to need to be changed two to three times per week.

Figure 4:
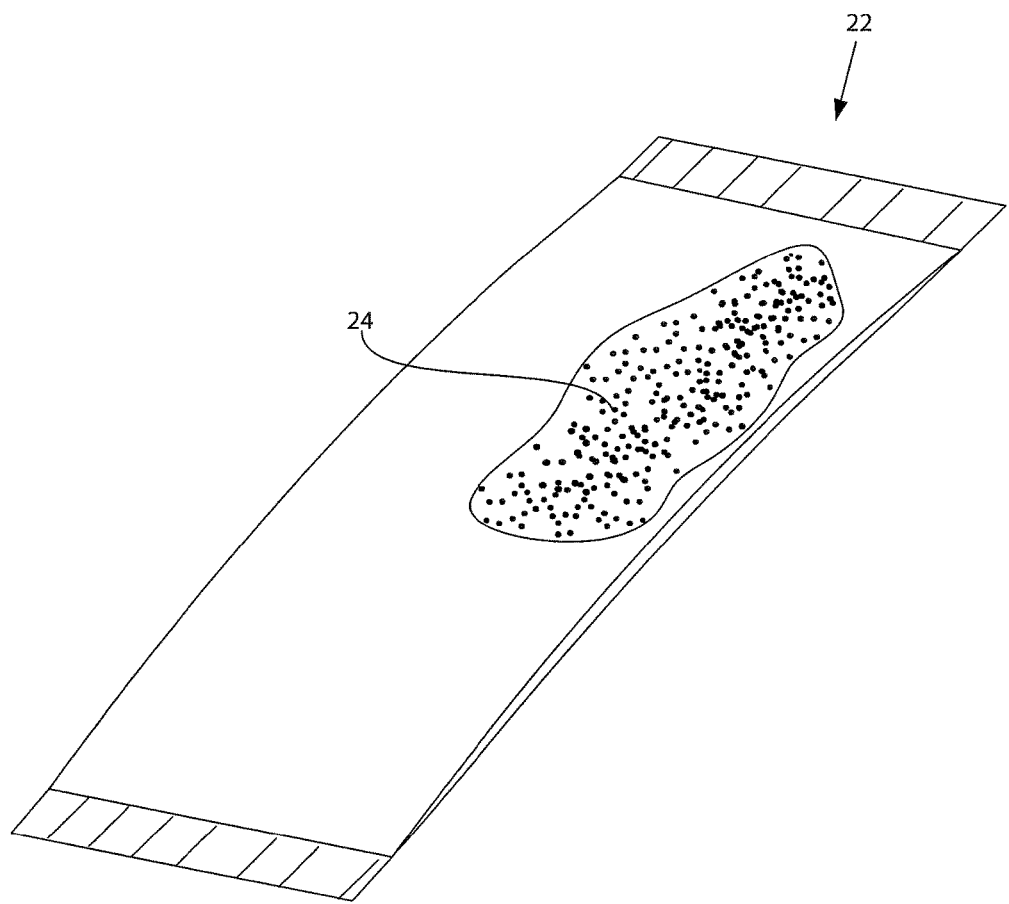
FIG. 4 is a perspective view of one example of a packet of the portable negative pressure wound therapy system according to FIG. 1.

The packet 22 is able to be housed within the container 12 and is at least partially soluble in an aqueous liquid. The plurality of surface cross-linked superabsorbent particles 24 are enclosed within the packet 22 and releasable upon at least partial dissolution of at least a portion of the packet in aqueous liquid. FIG. 4 shows examples of a packet 22 enclosing superabsorbent polymer particles 24. The packet 22 typically is placed inside of container 12 before a negative therapy wound pressure treatment is begun, however, may be added afterwards. In one example, the packet 22 is made of dissolvable polyvinyl alcohol; however, the packet made be made of any suitable water soluble film. The packet may be partially made of a paper type material and have a dissolvable portion. The dissolvable portion of packet 22 should have disintegration time and temperature suitable to the fluids in which it will be exposed. Another consideration is compatibility of the packet 22 with its contents. Packet 22 should provide for prolonged storage capacity without resulting in insolubility, rigidity or changes in packet 22 or its contents. Examples of such compatible packets 22 are dissolvable films that can be acquired from MonoSol, LLC, such as their models M7031, M7061, M8534, and M8900 (PXP6829) of water soluble film. Optionally, water soluble paper may be used. Packet 22 may be made entirely of a dissolvable packet, partially of a water soluble/permeable paper or may include a dissolvable portion. The dissolvability of packet 22 allows packet 22 to be placed into container 12 prior to introducing fluids into the container. The dissolvable packets 22 provide a cost effective way to eliminate risk of exposure for medical workers and/or patients and prevent excessive handling of the solidifier, container 12 or lid 26, either before or after fluids have been introduced and while they are still liquid. Such handling is necessary with powder or loose absorbents. Since the packet protects and can supply superabsorbent polymer particles to firmly solidify the exudate in the container, without the patient or personnel opening the container after the treatment has begun, then leakage or exposure becomes much less likely for NPWT devices, and portable and/or home NPWT devices. Additionally, firm solidification of the wastes minimizes the available fluid wastes that are able to seep out of the container and into the pump or controller, potentially damaging the most expensive parts of the NPWT system. A packet 22 may also be included within a container 12 prior to treatment and one side of the packet adhered to an interior portion of the container to maintain placement of the package. Any suitable adhesive or tape may be used that is compatible with the packet.

Enclosed within packet 22, shown in FIGS. 1 and 4, is a quantity of surface cross-linked superabsorbent particles 24, for example, Sodium Polyacrylate Polymer. Cross-linked superabsorbent particles are internally and surface cross-linked superabsorbent polymers. A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers have one or both of internal crosslinking and surface crosslinking. Surface crosslinking is any process that increases the crosslink density of the polymer matrix in the vicinity of the superabsorbent particle surface with respect to the crosslinking density of the particle interior. Surface cross-linked superabsorbent polymers of the present disclosure are available, for example, from Stockhausen, Inc. of Greensboro, N.C. or from Zappa Tec, LLC of McLeansville, N.C., as AP95.

In one example, after packet 22 with an enclosed polymer and/or polymer composition is placed inside container 12, then fluid 26 may be introduced without reopening or accessing the container. As liquid based biological waste is introduced into the container 12, packet 22 dissolves, releasing the solidifier. The solidifier 24 scatters throughout the aqueous liquid waste and the superabsorbent particles firmly solidify the liquid. The granular solidifier/composition becomes a gel-like substance as it solidifies the liquid. Due to the increased and maintained permeability of the superabsorbent polymer particles contained within the packet, fluid that arrives in container 12, even slowly over long periods, for example as a patient wound is treated over hours, days or weeks, is continually solidified. The packet housing the superabsorbent particles allows safe and effective pre-introduction of the solidifier before waste enters the container and prohibits gel-block due to maintained permeability of the superabsorbent particles even when a portion of the gel is already formed. The container for the NPWT system may even come pre-equipped with the solidifier packet already inside and potentially sealed, minimizing steps performed by the medical personnel and/or patient. The container may be disposable once fluid is solidified in the container over time and replaceable with another container having a solidifier packet for continued treatment to enhance sterile environments and safety for the patient.

A plurality of second particles may be combined with the superabsorbent polymer particles to make a solidification composition. The plurality of second particles may be inorganic, water-insoluble particles. In one embodiment, second particles may be hydrophilic fumed silica as is offered by Evonik Industries as AEROSIL® 200. While not the preferred embodiment, other additives such as silicates, kaolin, zeolites and bentonite may be used.

The plurality of second particles 18 may reside on the surface of the superabsorbent particles and become substantially interspaced between the superabsorbent particles. Second particles may be attracted to the superabsorbent particles by electrostatic forces. In some examples, the second particles may allow fuller and quicker liquid absorption by the superabsorbent particles by inhibiting full surface touching of the superabsorbent particles with one another. Additionally, the second particles may reduce attractive forces between the superabsorbent particles and reduce the likelihood of a film developing between superabsorbent particles that would inhibit permeability. Due to the presence of the second particles and the surface cross-linking of the superabsorbent particles, liquid flow channels may be maintained for a longer period of time between the superabsorbent particles. Thus, permeability of the gel is high as fluid is able to flow between the superabsorbent particles in the liquid flow channels, even after the particles begin to swell. Additionally, swellablity of the superabsorbent particles is increased due to the presence of the second particles. The liquid flow channels allow fluid to permeate the gel and flow to dry superabsorbent particles, thus further reducing the chance of occurrence of the previously known problem of gel block in the process of solidification of liquid medical wastes.

The absorbent composition may include superabsorbent polymer particles and a sanitizer. Adding a sanitizer assists in further neutralizing the contaminants in the liquid medical waste, reducing handling risk. Any suitable granular sanitizer may be used. The sanitizer, by way of example, may be sodium dichloro-s-triazinetrione dihydrate known as ACL® 56 Chlorinating Composition and available from OxyChem® of Texas. The absorbent composition reduces the chance of gel block and inadvertent exposure to hazardous bio-contaminants by allowing solidification without the need to interact with the inside of container 12 once a NPWT treatment begins. The sanitizer further minimizes exposure by neutralizing bio-contaminants within the waste fluid and solidified gel. The sanitizer that is added may be any suitable agent that destroys bacteria, fungi, viruses, organic matter and/or waste contaminants without interfering with the packet integrity and the solidifier. Dissolvable films were tested to determine example dissolvable packs that maintain proper functionality with the addition of the sanitizer. Similar considerations as discussed above for the dissolvable film packs would apply here as well. The sanitizer creates a different chemical environment within the packets and may cause greater instability over time in the packets typically used for housing superabsorbent particles alone. Other examples of compatible packets for use with superabsorbent particles mixed with sanitizer are dissolvable films that can be acquired from MonoSol, LLC, such as their models M7031 and M8900 (PXP6829) of water soluble film. Another packet material able to suitably accommodate the addition of a sanitizer to the packet is, the GA40 film manufactured by Aicello American Corporation. Through testing, Applicant has determined that this film is effective for use with the superabsorbent particles and sanitizing agents.

Another factor that has minimized the use of NPWT devices both in hospitals and with portable devices at home is the odor that can accompany the treatment. Filters have been tried and occasionally charcoal additives included in the container. The exudate collected in collection vessels during a NPWT treatment can provide a breeding ground fertile for growth of biological organisms, such as bacteria. The exudate and the biological organisms themselves can either and/or both create an extremely odorous byproduct environment that makes the use of NPWT devices extremely unpleasant. The odor can increase over time and become intolerable, especially in NPWT treatments that, not uncommonly, last for hours, days, weeks or longer. The addition of the sanitizer to the superabsorbent polymer particles not only disinfects the exudate, reducing odors, but also prohibits development of a biological organism breeding ground within the container 12. Alternatively, disposing of the container once in use for a period and continuing the treatment with fresh container may assist with sanitation and odor control for the patient.

Additionally, this invention may be a liquid solidification system for reducing gel block in negative pressure wound therapy treatment systems, including a NPWT device, a packet and a liquid solidifier. The packet may be entirely dissolvable in fluids or may contain a dissolvable section. The liquid solidifier includes a plurality of surface cross-linked superabsorbent polymer particles that maintain fluid permeability during solidification of waste fluids. The packet may optionally be a bottle or any other suitable type of container. The system may include a sanitizer. The system may include a population of second particles.

As many medical treatments are, wound care and NPWT can be expensive. Therefore, it is beneficial if the treatments can be made more effective with less waste of supplies and increased safety. Applicant's invention minimizes the amount of solidifier necessary to reach firm solidification of the waste in a container and also minimizes the need to change out the container more often. While it is a benefit of Applicant's invention to be able to have the solidifier contained and protected in the packet and to be added before the treatment begins, it is also possible to begin with minimal determined amounts of solidifier and add more in additional packets if more fluid than originally projected is collected, or if the treatment needs to proceed longer without interruption. Particularly in portable and home use NPWT devices, as little as about 5 to 9 grams of superabsorbent polymer particles may be placed in packets and used for solidification of the entire volume of the waste container. Variable amounts of polymer may be allocated depending on the volume and usage. Packets can be fitted accordingly.

In other examples, 5 to 22 grams or more of superabsorbent particles may be packeted. Typically, the liquid solidification system proportionally may include about 20 grams of the superabsorbent polymer particles per 1000 cc of fluid to be solidified. By weight/weight % a ratio of about 0.5% to 1.5% of the second particles per the superabsorbent polymer particles, preferably 1% second particles may be added.

In one example, the system may include between 20 and 40 grams of the superabsorbent polymer particles per 1000 cc of fluid to be solidified. Additionally, the liquid solidification system may further include by weight/weight %, a ratio of about 5% to 15% of sanitizer per superabsorbent polymer particles, preferably 10%. When the sanitizer is added to the liquid solidification system, the system may include an additional by weight/weight % a ratio of about 10% to 20% of superabsorbent polymer particles to the original grams of superabsorbent polymer particles. The additional superabsorbent polymer was found to be beneficial to the solidification process when the sanitizer was added to ensure firm solidification in the presence of the sanitizer.

The invention may further be a method of solidifying liquid medical waste in a negative pressure wound therapy system comprising the steps of: housing a population of cross-linked superabsorbent polymer particles in a dissolvable film packet; sizing the packet to fit within a container; including an amount of particles in the population sufficient to solidify the volume of liquid accommodated by the container.

Prior systems and methods of releasing superabsorbent polymer, including internally cross-linked superabsorbent polymer particles, have been found to suffer from gel block due to the rapid swelling of the particles. Gel blocking occurs when the body of the absorbent forms a barrier layer of gel that keeps further liquid from contacting dry absorbent on a side of the gel away from the liquid. Such gel blocking may prevent the complete absorption of the liquid since the liquid to be absorbed is kept away from the dry absorbent by the gel barrier. Surface cross-linked superabsorbent polymers have been found to increase the strength of the polymer-gel in sanitary articles such as diapers; however, increasing gel strength often decreases permeability, swellability and retention capacity of the superabsorbent polymer. While successfully applied in sanitary articles, absorption of medical fluids has the additional concern of gel block.

At the end of or during a NPWT procedure where liquid medical waste is gathered, the contents are turned into a firm gel, and the container can be disposed of sanitarily with less of a threat of spillage or patient and/or personnel exposure. Typically, the container 12 with its gelled waste contents is disposed of as a standard biohazard, without opening the container 12. Post-procedure cleanup is streamlined, sanitary and time saving. The liquid solidifier in the packet is a much more efficiently packaged product as it is durable and easy to handle. Without bottles or solidifier to keep safe outside of the container prior to treatment, no excess solid waste is generated and storage capacity is minimal. However, as previously discussed, use of the particle combinations dispensed from bottles or other containers is within the scope of the invention.

The particle and packet combination provides full solidification, irrespective of how quickly fluid is introduced.

The particle combination inhibits the formation of gel block prior to firm solidification.

The particle combination reduces the time and risk of adding solidifier after waste fluid is introduced and the time and risk involved with post procedure handling.

The particle combination as packaged in the packet saves on storage space.

The packet and particle combination, along with sanitizer, minimizes the odor and risk associated with NPWT waste collection.

Certain modifications and improvements will occur to those skilled in the art upon reading the foregoing description. It should be understood that all such modifications and improvements have been omitted for the sake of conciseness and readability, but are properly within the scope of the following examples. For example, although the primary intended use is for liquid medical waste, other aqueous liquids could be solidified. Also, although the film is preferably all dissolvable, it is within the scope of the invention to make only parts dissolvable.

I claim:

1. A disposable negative pressure wound therapy waste collection system comprising:
    a container operable to receive fluid from a wound site and in communication with a vacuum tube, wherein the vacuum tube connects to a vacuum control having a negative pressure source,
    a wound covering connecting to the vacuum tube so that the negative pressure source is able to exert a negative pressure on the wound site through the covering when the covering is applied to the site,
    a packet able to be housed within the container, the packet being at least partially soluble in an aqueous liquid, and
    a plurality of surface cross-linked superabsorbent particles enclosed within the packet and releasable upon dissolution of at least a portion of the packet in the aqueous liquid,
    wherein the plurality of the surface cross-linked superabsorbent particles maintain permeability and prohibit gel-block of the aqueous liquids when the aqueous liquids are introduced slowly within the container over a period of at least an hour.

2. The system of claim 1, including second particles.

3. The system of claim 2, wherein the second particles are inorganic non-soluble particles.

4. The system of claim 3, wherein the second particles are fumed silica.

5. The system of claim 1, further including a sanitizer.

6. The system of claim 5, wherein the sanitizer is granular chlorine.

7. A system for solidification of liquid medical waste for use in connection with a container configured to receive an aqueous liquid from a NPWT device to be solidified comprising:
- an absorbent composition, the absorbent composition being granular and including a plurality of surface cross-linked superabsorbent particles surface cross-linked to maintain permeability and configured to prohibit gel-block during the introduction of aqueous liquids, and
- a packet enclosing the absorbent composition, the packet being at least partially soluble in the aqueous liquid to be solidified so that the absorbent composition is released upon dissolution of the packet,
- wherein the aqueous liquids are slowly introduced into the container over a time period into a patient controlled collection device and the absorbent composition is configured to maintain a firm solidification over the entire period of time that fluids are collected and introduced into the patient controlled collection device.

8. The system for the solidification system of claim 7, including a wound covering and a negative pressure source.

9. The system for solidification as claimed in claim 8, wherein the packet is made of dissolvable polyvinyl alcohol.

10. A Negative Pressure Wound Therapy solidification system for reducing gel block, the system comprising:
- a container for collecting liquid wastes entering the container over a time period of at least an hour;
- a packet configured to fit within the container and to allow a liquid penetration; and
- a solidifier for liquids that is initially located within the packet, the solidifier comprising:
  - an amount of a superabsorbent polymer particles to firmly solidify the volume of liquid wastes able to be held by the container, wherein a plurality of liquid flow channels maintain permeability to allow for firm solidification of the volume of fluid held by the container.

11. The liquid solidification system of claim 10, wherein the solidifier for liquid further includes by weight/weight %, a ratio of about 0.5% to 1.5% of a portion of second particles.

12. The liquid solidification system of claim 10, further including by weight/weight % ratio of about 5% to 15% of sanitizer.

13. The liquid solidification system of claim 12, wherein a plurality of liquid flow channels maintain permeability to allow for firm solidification in under 5 minutes.

14. The liquid solidification system of claim 10, wherein a plurality of liquid flow channels maintain permeability to allow for firm solidification of the volume of fluid held by the container at a rate chosen from 5 to 10 minutes.

15. A solidification method for Negative Pressure Wound Therapy waste fluids comprising:
- including a container operable to receive fluid from a wound site and in communication with a Negative Pressure Wound Therapy device,
- having the container in communication with a vacuum tube,
- providing a negative pressure source,
- allowing a wound covering to connect to the vacuum tube so that the negative pressure source is able to exert a negative pressure on the wound site through the covering when the covering is applied to the site, and
- including a packet in the container to be housed within the container, the packet being at least partially soluble in an aqueous liquid and having a plurality of surface cross-linked superabsorbent particles enclosed within the packet that are releasable upon dissolution of at least a portion of the packet in the aqueous liquid,
- selecting the surface cross-linked superabsorbent particles to maintain permeability and prohibit gel-block during introduction of the waste fluids over the course of a Negative Pressure Wound Therapy treatment such that the waste fluids entering the container are firmly solidified.

16. The method of claim 15, including a sanitizer housed along with the particles inside the packet.

17. A method of solidification for Negative Pressure Wound Therapy (NPWT) systems comprising:
- selecting a quantity of cross-linked superabsorbent particles that maintain a state of permeability upon solidification and during the introduction of the aqueous liquids over an entire period of time during which the cross-linked super absorbent particles remain in the NPWT system,
- determining the quantity based upon a volume of liquid wastes to be solidified within a NPWT container during a NPWT treatment,
- encasing the quantity inside an at least partially water soluble packet, and
- sizing the water soluble packet to fit inside the NPWT container.

18. The method of claim 17, including providing a quantity of cross-linked superabsorbent particles adapted to achieve firm solidification of liquid wastes.

19. The method of claim 18, including housing sanitizer along with the quantity of particles inside the packet.

20. The method of claim 18, including allowing firm solidification of gathered fluids entering the container in a patient controlled collection device for a NPWT treatment.

* * * * *